(12) United States Patent
Murata et al.

(10) Patent No.: US 8,765,427 B2
(45) Date of Patent: Jul. 1, 2014

(54) ETHANOL PRODUCTION FROM MANNITOL USING YEAST

(75) Inventors: Kousaku Murata, Kyoto (JP); Shigeyuki Kawai, Kyoto (JP); Hiroshi Oda, Ibaraki (JP); Keishi Iohara, Ibaraki (JP)

(73) Assignee: Maruha Nichiro Holdings, Inc., Tokyo (JP)

( * ) Notice: Subject to any disclaimer, the term of this patent is extended or adjusted under 35 U.S.C. 154(b) by 0 days.

(21) Appl. No.: 13/408,489

(22) Filed: Feb. 29, 2012

(65) Prior Publication Data

US 2013/0059356 A1 Mar. 7, 2013

(30) Foreign Application Priority Data

Sep. 2, 2011 (JP) ................................. 2011-191971

(51) Int. Cl.
*C12P 7/06* (2006.01)
*C12P 7/14* (2006.01)

(52) U.S. Cl.
USPC .......................................................... 435/162

(58) Field of Classification Search
USPC .......................................................... 435/162
See application file for complete search history.

(56) References Cited

U.S. PATENT DOCUMENTS

2012/0220004 A1   8/2012   Murata et al.

FOREIGN PATENT DOCUMENTS

| JP | 2006-280362 | 10/2006 |
|----|-------------|---------|
| JP | 2011-041493 | 3/2011 |
| JP | 2011-121042 | 6/2011 |
| WO | 2011/024858 | 3/2011 |

OTHER PUBLICATIONS

Horn et al., "Ethanol Production from Seaweed Extract", 2000, 25:249-254.*
Breuer et al., "*Debaryomyces hansenii*—an extremophilic yeast with biotechnological potential", Yeast 2006; 23: 415-437.*
Adams et al., "Fermentation study on *Saccharina latissima* for bioethanol production considering variable pre-treatments", J Appl Phycol (2009) 21:569-574.*
Anri Ota, et al., "Bioethanol production from mannitol by the yeast", Abstract of the 63$^{rd}$ Annual Meeting of the Society for Biotechnology, 2Ap07, Aug. 25, 2011, 6 pages (English Translation).
Anri Ota, et al., "Searching for yeast that produces ethanol from mannitol", Abstracts of the Annual Meeting of Japan Society for Bioscience, Biotechnology and Agrochemistry, 3B03a12, 2011, 5 pages (With English Translation).
Office Action issued Jan. 21, 2014, in Japanese Patent Application No. 2011-191971, filed Sep. 2, 2011.
David E. Quain, et al., "Growth and Metabolism of Mannitol by Strains of Saccharomyces cerevisiae", Journal of General Microbiology (1987), 133, 1675-1684.

* cited by examiner

*Primary Examiner* — Suzanne M Noakes
(74) *Attorney, Agent, or Firm* — Oblon, Spivak, McClelland, Maier & Neustadt, L.L.P.

(57) ABSTRACT

This invention provides a method for producing ethanol from mannitol using yeast and a yeast strain that produces ethanol from mannitol. The method for producing ethanol from mannitol comprises culturing yeast strains capable of mannitol assimilation and ethanol production from mannitol in a medium containing mannitol.

13 Claims, 18 Drawing Sheets

Strain

BY    NB      BY    NB
Mannitol      Glucose

ETHANOL PRODUCTION FROM MANNITOL USING YEAST

TECHNICAL FIELD

The present invention relates to a method for producing ethanol from mannitol using yeast and a yeast strain that produces ethanol from mannitol.

BACKGROUND ART

Marine biomass, such as large marine algae, is a promising starting material for biofuel. Examples of major reasons therefor include: (i) large marine algae exhibit higher productivity than terrestrial biomass; (ii) unavoidable problems that arise when cultivating terrestrial biomass (e.g., irrigation or dressing) can be avoided since cropland is not necessary; and (iii) large marine algae are lignin-free. Major examples of large marine algae include green algae, red algae, and brown algae. Among them, at least red algae and brown algae contain significant amounts of carbohydrates. *Gelidium amansii*, which is one type of red algae, contains 17% cellulose (glucose) (w/w (dry weight basis); hereafter, "w/w" refers to dry weight unless otherwise specified) and 58.6% (w/w) agar (25.6% galactose and 33% 3,6-anhydrogalactose). Brown algae contain 40% (w/w) alginic acid, 30% (w/w) mannitol, and 30% (w/w) laminarin at maximum. Therefore, biofuel production using large marine algae as starting materials requires the establishment of a technique for converting such carbohydrate components into biofuel.

Alginic acid is a linear acidic polysaccharide composed of β-D-mannuronic acid (M) and its C5-epimer (i.e., α-L-guluronic acid (G)). A constitutive monosaccharide has a poly-M, poly-G, or poly-MG structure. Mannitol is a sugar alcohol corresponding to mannose, and it is oxidized via the action of mannitol dehydrogenase and then converted into fructose (FIG. 1) (refer to Non-Patent Documents 1 and 2). Laminarin is composed of β-(1,3)-D-glucan having a 3-(1,6)-branching structure (refer to Non-Patent Documents 3 and 4). The present inventors have already constructed a system for producing ethanol from alginic acid using the ethanol-producing *Sphingomonas* sp. A1 strain (hereafter referred to as "the ethanol-producing A1 strain") and succeeded in producing 1.3% (w/v) ethanol (refer to Non-Patent Document 5). Such technique is an only one technique for producing biofuel from alginic acid. There have been a few examples of ethanol production from laminarin. However, there has been a report regarding ethanol production via laminarin decomposition by three yeast strains (i.e., *Kluyveromyces marxianus*, *Pacchysolen tannophilus*, and *Phicia angophorae*) (refer to Non-Patent Document 1), as well as a report regarding ethanol production using a yeast strain (i.e., *Saccharomyces cerevisiae*) from a product of laminarin decomposed by a laminarin-degrading enzyme (i.e., laminarise) (Adams et al., 2009). Regarding production of ethanol from mannitol, it was reported that the bacterial strains (i.e., *Zymobacter palmae* and *Escherichia coli* KO11) had produced about 1.3% (w/v) and 2.6% (w/v) ethanol from 3.8% (w/v) and 9.0% (w/v) mannitol with production efficiency of 0.38 g and 0.41 g of ethanol (mannitol)$^{-1}$, respectively (refer to Non-Patent Documents 1 and 6). From the viewpoint of ethanol production, however, yeast strains are considered to be advantageous over bacterial strains in various respects, such as tolerance to ethanol or fermentation inhibitors (refer to Non-Patent Document 7) (Hughes and Qureshi, 2010). In fact, *Z. palmae* and *E. coli* KO11 inhibit growth in the presence of 5% (w/v) ethanol (refer to Non-Patent Documents 8 and 9). However, there has been very little research regarding ethanol production from mannitol using yeast. Such research is limited to a report to the effect that a yeast strain (*S. cerevisiae* polyploid BB1) produces about 0.5% ethanol from 5% (w/v) mannitol (refer to Non-Patent Document 2) and a report to the effect that only *P. angophorae* among the laminarin-degrading yeast strains mentioned above (i.e., *K. marxianus*, *P. tannophilus*, and *P. angophorae*) produces about 1.0% (w/v) ethanol from 4% (w/v) mannitol with production efficiency of 0.40 g of ethanol (mannitol)$^{-1}$ (refer to Non-Patent Document 1). In research involving the use of *P. angophorae*, ethanol production from an algal extract comprising both mannitol and laminarin and the influence of the amount of oxygen supplied on the speed of mannitol and laminarin consumption have been reported (refer to Non-Patent Document 1). However, only a few reports have been made regarding mannitol metabolism using yeast. It has been reported that yeast strains (*S. cerevisiae*) are classified as those capable of mannitol assimilation (e.g., the polyploid BB1 strain and the monoploid A184D strain) and those incapable of mannitol assimilation (or having a very weak capacity for assimilation, such as the polyploid BB2 strain and the haploid S288C and Sc41 YJO strains). It has also been reported that mannitol assimilation using *S. cerevisiae* requires oxygen and yeast strains growing in a mannitol-containing medium exhibit a high degree of respiratory activity (refer to Non-Patent Documents 2 and 10). The monoploid strain S288C is the first strain the genome sequence of which was determined (refer to Non-Patent Document 11).

In order to achieve practical use of ethanol production from mannitol using yeast, it is essential to search for yeast strains exhibiting a high degree of ethanol productivity from mannitol or various other excellent properties, or to breed such strains and to establish optimal conditions for exerting a high degree of ethanol productivity. In order to establish an ethanol production system from marine biomass, further, a technique for converting all of the constituents into ethanol is necessary. In the case of brown algae, it is necessary to establish a technique for converting alginic acid, mannitol, laminarin, and the like into ethanol. Known systems for production of ethanol from alginic acid are limited to a single system involving the use of the ethanol-producing A1 strain described above (refer to Non-Patent Document 5). The A1 strain is not capable of mannitol or laminarin assimilation (unpublished data). The capacity for alginic acid assimilation is known only in a limited number of organisms, such as the *Sphingomonas* sp. A1 strain.

PRIOR ART DOCUMENTS

Non-Patent Documents

Non-Patent Document 1: Horn, et al., 2000, J. Ind. Microbiol. Biotechnol. 25, 249-254

Non-Patent Document 2: Quain and Boulton, 1987, J. Gen. Microbiol. 133, 1675-1684

Non-Patent Document 3: Nelson and Lewis, 1973, Carbohydr. Res. 33, 63-74

Non-Patent Document 4: Zvyagintseva et al., 1999, Carbohydr. Res. 322, 32-39

Non-Patent Document 5: Takeda et al., 2011, Energy Environ. Sci. 4, 2575-2581

Non-Patent Document 6: Kim et al., 2011, Bioresour. Technol. 102, 7466-7469

Non-Patent Document 7: Hughes and Qureshi, 2010, Biomass to biofuels: Strategies for global industries, pp. 55-69

Non-Patent Document 8: Okamoto et al., 1994, Biosci. Biotech. Bioch. 58, 1328-1329

Non-Patent Document 9: Yomano et al., 1998 J. Ind. Microbiol. Biotechnol. 20, 132-138
Non-Patent Document 10: Perfect et al., 1996, J. Bacteriol. 178, 5257-5262
Non-Patent Document 11: Goffeau et al., 1996, Science 274, 546, 563-547

SUMMARY OF THE INVENTION

Object to be Attained by the Invention

The present invention is intended to provide a method for producing ethanol from mannitol using yeast and a yeast strain that produces ethanol from mannitol.

Means for Attaining the Object

The present inventors considered that two-step fermentation that produces ethanol with the use of yeast strains capable of mannitol and laminarin assimilation from mannitol and laminarin contained in the residue of ethanol fermentation from alginic acid using ethanol-producing A1 strains would facilitate effective application of brown-algae-derived biomass to ethanol production. Thus, the present inventors first aimed at realization thereof and searched for yeast strains exhibiting the high ethanol productivity from mannitol.

A technique for producing ethanol from alginic acid, mannitol, and laminarin, which are major components of marine biomass (brown algae), is essential for the production of biofuel (ethanol) from such marine biomass. A system for producing ethanol from alginic acid using the ethanol-producing *Sphingomonas* sp. A1 strain has already been established (Takeda et al., 2011, Energy Environ. Sci. 4, 2575-2581). Conversion of mannitol or laminarin contained in a residue after ethanol fermentation from alginic acid into ethanol using the strain of interest is an instance of effective use of a major component of brown algae. The present inventors discovered six ethanol-producing strains capable of mannitol assimilation among the stock yeast strains. Among such strains, the *Saccharomyces paradoxus* NBRC 0259 strain does not exhibit ethanol productivity from laminarin; however, such strain exhibits preferable properties, such as high ethanol productivity from glucose and mannitol, ethanol tolerance, and viability in a residue of ethanol fermentation from alginic acid. While the other five strains exhibited ethanol productivity from laminarin, other properties of such strains were inferior to those of the NBRC 0259 strain. The NBRC 0259 strain produced 37.6 g/l (3.8% w/v) ethanol from 10% (w/v) mannitol at maximum under a microaerophilic environment attained via shaking at 95 strokes per min (spm). The influence of NaCl on ethanol fermentation was insignificant. Ethanol was also produced from mannitol in the residue of the ethanol fermentation from alginic acid. This strain was considered to be useful for the production of ethanol from marine biomass.

Specifically, the present invention is as follows.

[1] A method for producing ethanol using mannitol as a starting material comprising culturing yeast strains capable of mannitol assimilation and ethanol production from mannitol in a medium containing mannitol.

[2] The method for producing ethanol from mannitol according to [1], wherein the yeast strains capable of mannitol assimilation and ethanol production from mannitol have at least one property selected from among the properties (1) to (3) below:

(1) ethanol tolerance;
(2) viability in the residue used when ethanol is produced from brown algae as a starting material using microorganisms capable of alginic acid assimilation; and
(3) aggregability in the presence of glucose.

[3] The method for producing ethanol from mannitol according to [1] or [2], wherein the yeast strains capable of mannitol assimilation and ethanol production from mannitol are selected from the group consisting of *Saccharomyces paradoxus*, *Debaryomyces hansenii*, *Kuraishia capsulata*, *Ogataea glucozyma*, and *Ogataea minuta*.

[4] The method for producing ethanol from mannitol according to [3], wherein the yeast strains capable of mannitol assimilation and ethanol production from mannitol are selected from the group consisting of the *Saccharomyces paradoxus* NBRC 0259 strain, the *Debaryomyces hansenii* NBRC 0794 strain, the *Kuraishia capsulata* NBRC 0721 strain, the *Kuraishia capsulata* NBRC 0974 strain, the *Ogataea glucozyma* NBRC 1472 strain, and the *Ogataea minuta* NBRC 1473 strain.

[5] The method according to any of [1] to [4], wherein the yeast strains capable of mannitol assimilation and ethanol production from mannitol are cultured such that 0.1% (w/v) or more ethanol accumulates in the medium.

[6] The method according to [5], wherein the yeast strains capable of mannitol assimilation and ethanol production from mannitol are cultured such that 3% (w/v) or more ethanol accumulates in the medium.

[7] A method for producing ethanol from mannitol as a starting material in a residue after ethanol is produced from brown algae, using microorganisms capable of alginic acid assimilation and ethanol production from alginic acid, which comprises adding yeast strains capable of mannitol assimilation and ethanol production from mannitol to the residue of the starting material, and culturing the yeast strains.

[8] The method for producing ethanol from mannitol in the residue according to [7], wherein the yeast strains capable of mannitol assimilation and ethanol production from mannitol have at least one property selected from among the properties (1) to (3) below:

(1) ethanol tolerance;
(2) viability in the residue used when ethanol is produced from brown algae as a starting material using microorganisms capable of alginic acid assimilation; and
(3) aggregability in the presence of glucose.

[9] The method for producing ethanol from mannitol as a starting material in the residue according to [7] or [8], wherein the yeast strains capable of mannitol assimilation and ethanol production from mannitol are *Saccharomyces paradoxus* strains.

[10] The method for producing ethanol from mannitol as a starting material in the residue according to [9], wherein the yeast strains capable of mannitol assimilation and ethanol production from mannitol are *Saccharomyces paradoxus* NBRC 0259 strain.

[11] A method for producing ethanol from brown algae as a starting material comprising:

(i) culturing microorganisms capable of alginic acid assimilation and ethanol production from alginic acid using brown algae as a starting material to produce ethanol from alginic acid; and (ii) adding yeast strains capable of mannitol assimilation and ethanol production from mannitol to the residue of the starting material used for culture in (i) and culturing the yeast strains.

[12] The method for producing ethanol from brown algae as a starting material according to [1,1], wherein the yeast strains capable of mannitol assimilation and ethanol production from mannitol have at least one property selected from among the properties (1) to (3) below:

(1) ethanol tolerance;
(2) viability in the residue used when ethanol is produced from brown algae as a starting material using microorganisms capable of alginic acid assimilation; and
(3) aggregability in the presence of glucose.

[13] The method for producing ethanol from brown algae as a starting material according to [1,1] or [1,2], wherein the yeast strains capable of mannitol assimilation and ethanol production from mannitol are *Saccharomyces paradoxus* strains.

[14] The method for producing ethanol from brown algae as a starting material according to [1,3], wherein the yeast strains capable of mannitol assimilation and ethanol production from mannitol is *Saccharomyces paradoxus* NBRC 0259 strain.

This description includes part or all of the contents as disclosed in the description and/or drawings of Japanese Patent Application No. 2011-191971, which is a priority document of the present application.

Effects of the Invention

With the use of the yeast strains capable of mannitol assimilation and ethanol production from mannitol according to the present invention, ethanol can be produced using mannitol as a starting material. The residue of ethanol production from marine-derived biomass, and in particular, a large quantity of polysaccharide alginic acid contained in brown algae, contains a large quantity of mannitol, and such residue can be effectively used for ethanol production.

BRIEF DESCRIPTION OF THE DRAWINGS

FIG. 2C-1 shows growth of ethanol-producing yeast strains capable of mannitol assimilation in a laminarin synthetic liquid medium (white), a mannitol synthetic liquid medium (fine parallel lines), and a glucose-synthetic liquid medium (black). The yeast strain numbers are the same as those shown in FIG. 2B. The *S. paradoxus* NBRC 0259 strain (Strain 1) exhibited strong aggregability in a glucose-synthetic liquid medium (*).

FIG. 2C-2 shows ethanol productivity of ethanol-producing yeast strains capable of mannitol assimilation in a laminarin synthetic liquid medium (white), a mannitol synthetic liquid medium (fine parallel lines), and a glucose-synthetic liquid medium (black). The right scale shows the concentration of glucose-derived ethanol and the left scale shows that of laminarin- or mannitol-derived ethanol. The yeast strain numbers are the same as those shown in FIG. 2B.

FIG. 4A-1 shows growth of six ethanol-producing yeast strains capable of mannitol assimilation. The yeast strains were subjected to shake culture at 95 spm in a 50-ml triangular flask containing 25 ml of YPM liquid medium. The yeast strains are represented by the following symbols: ♦: *S. paradoxus* NBRC 0259; ▲: *K. capsulata* NBRC 0721; X: *K. capsulata* NBRC 0974; ●: *O. glucozyma* NBRC 1472; +: *O. minuta* NBRC 1473; and ■: *D. hansenii* NBRC 0794.

FIG. 4A-2 shows ethanol productivity of six ethanol-producing yeast strains capable of mannitol assimilation. The yeast strains were subjected to shake culture at 95 spm in a 50-ml triangular flask containing 25 ml of YPM liquid medium. Symbols indicating the yeast strains are the same as those used in FIG. 4A-1.

FIG. 5C-1 shows the influence of the extent of shaking on viability in YPM (▲●■) and YPD (□○) liquid media (▲: 145 spm; ●○: 95 spm; ■□: 0 spm). The NBRC 0259 ρ⁺ strain derived from YPM solid medium were precultured at 95 spm in YPM liquid medium for 24 hours, and the precultured cells were sowed to initiate culture. The NBRC 0259 strain exhibited aggregability in a glucose-synthetic liquid medium (*).

FIG. 5C-2 shows the influence of the extent of shaking on ethanol productivity in YPM (▲●■) and YPD (□○) liquid media (▲: 145 spm; ●○: 95 spm; ■□: 0 spm). The NBRC 0259 ρ⁺ strain derived from YPM solid medium were precultured at 95 spm in YPM liquid medium for 24 hours, and the precultured cells were sowed to initiate culture. These strains did not exhibit ethanol productivity at 145 spm (▲).

EMBODIMENTS FOR CARRYING OUT THE INVENTION

Hereafter, the present invention is described in detail.

Figure 1:
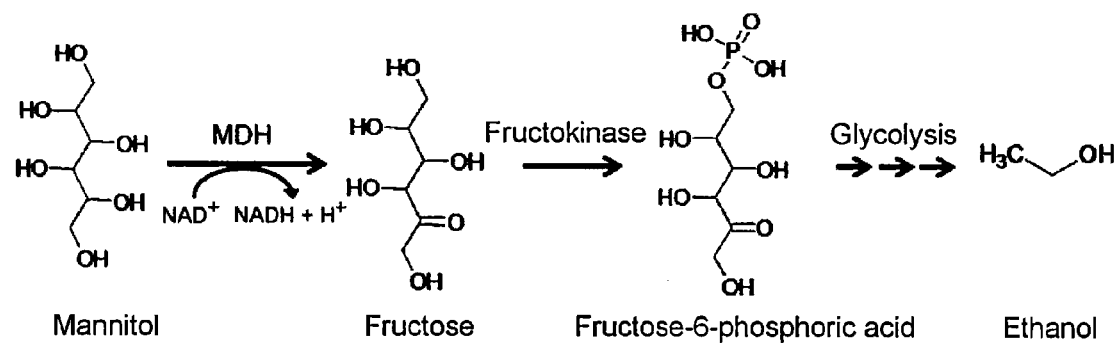
FIG. 1 shows the putative pathway of mannitol assimilation using yeast.

The yeast strains of the present invention are capable of mannitol assimilation and ethanol production from mannitol. The reaction for producing ethanol from mannitol is shown in FIG. 1.

Examples of the yeast strains capable of producing ethanol from mannitol of the present invention include *Saccharomyces paradoxus* NBRC 0259, *Debaryomyces hansenii* NBRC 0794, *Kuraishia capsulata* NBRC 0721, *Kuraishia capsulata* NBRC 0974, *Ogataea glucozyma* NBRC 1472, and *Ogataea minuta* NBRC 1473. These strains are conserved at the Biological Resource Center, the National Institute of Technology and Evaluation (NITE), the Incorporated Administrative Agency (NBRC), and they are available therefrom.

In addition, the yeast strains capable of mannitol assimilation and ethanol production from mannitol of the present invention preferably have ethanol tolerance. Ethanol tolerance can be imparted to strains by tolerizing strains against ethanol. For example, random mutation is induced via conditioned culture in an ethanol-containing medium and via ultraviolet application, so that ethanol-tolerant strains can be obtained. The yeast strains of the present invention can grow in the presence of 0.85% (w/v) or more, preferably 1.7% or more, more preferably 3% (w/v) or more, more preferably 5% (w/v) or more, more preferably 6% (w/v) or more, more preferably 7% (w/v) or more, more preferably 8% (w/v) or more, and particularly preferably 8.5% (w/v) or more ethanol.

Further, the yeast strains capable of mannitol assimilation and ethanol production from mannitol of the present invention preferably have viability in a residue of ethanol fermentation from alginic acid. The viability in a residue of ethanol fermentation is deduced to be associated with tolerance to growth inhibitors. The term "residue of ethanol fermentation from alginic acid" used herein refers to a residue of starting materials when ethanol is produced from starting materials such as alginic acid-containing brown algae using microorganisms capable of alginic acid assimilation. Such residue contains mannitol and laminarin, which are major components of brown algae other than alginic acid. An example of a microorganism capable of alginic acid assimilation is the *Sphingomonas* sp. A1 strain. Ethanol can be produced from alginic acid using the ethanol-producing *Sphingomonas* sp. A1 strain resulting from introduction of the gene encoding enzymes (pyruvic acid decarboxylase and alcohol dehydrogenase) associated with ethanol production of bacteria (e.g., *Zymomonas mobilis*) into the A1 strain. The ethanol-producing *Sphingomonas* sp. A1 strain is described in detail in Takeda et al., 2011, Energy Environ. Sci. 4, 2575-2581 or WO 2011/024858. The yeast strains capable of mannitol assimilation and ethanol production from mannitol of the present invention are capable of additional ethanol production from a mannitol-containing residue remaining after ethanol is produced from brown algae using the ethanol-producing *Sphingomonas* sp. A1 strain described above. Thus, a large quantity of ethanol can be produced with the effective use of brown algae, which is marine biomass. Ethanol may be produced from mannitol via two-step fermentation with the use of a residue after ethanol is produced using brown algae as a starting material from alginic acid using microorganisms capable of producing ethanol from alginic acid. Alternatively, the microorganisms capable of producing ethanol from alginic acid and the yeast strains capable of mannitol assimilation and ethanol production from mannitol of the present invention may be simultaneously added to the brown-algae-derived starting material to simultaneously produce ethanol from alginic acid and mannitol. Further, microorganisms capable of laminarin assimilation and ethanol production from laminarin may be simultaneously added. Alternatively, ethanol can be produced from brown algae as a starting material via two-step fermentation. That is, ethanol is first produced from mannitol using yeast strains capable of mannitol assimilation and ethanol production from mannitol, and ethanol is further produced from alginic acid in the residue using microorganisms capable of ethanol production.

Further, the yeast strains capable of mannitol assimilation and ethanol production from mannitol of the present invention preferably have aggregability in the presence of glucose. The term "aggregability" used herein refers to the capacity of cells for reversibly aggregating with each other to form aggregates (which may be occasionally referred to as "flocks"). Strains having aggregability are advantageous in terms of ease of recovery of yeast strains. Specifically, the cost, energy, and labor required for recovery can be reduced, since separation procedures, such as centrifugation, are not necessary. Also, such strains have improved ethanol tolerance because of aggregability imparted thereto (Zhao and Bai, 2009, Biotechnol. Adv. 27, 849-856). The yeast strains of the present invention have aggregability in the presence of less than 7%

(w/v), preferably 6% (w/v) or less, more preferably 5% (w/v) or less, and particularly preferably 3% (w/v) or less ethanol.

As described above, the yeast strains capable of mannitol assimilation and ethanol production from mannitol of the present invention further have at least one of properties (1) to (3) below (i.e., property (1), property (2), property (3), properties (1) and (2), properties (1) and (3), properties (2) and (3), or properties (1), (2), and (3)):

(1) ethanol tolerance;
(2) viability in the residue used when ethanol is produced from brown algae as a starting material using microorganisms capable of alginic acid assimilation; and
(3) aggregability in the presence of glucose.

Among the above 6 yeast strains, the *Saccharomyces paradoxus* NBRC 0259 strain, which is satisfactory in terms of ethanol productivity, ethanol tolerance, viability in a residue of ethanol fermentation from alginic acid, and aggregability in the presence of glucose, is preferable. The NBRC 1472 *Ogataea glucozyma* strain, which is satisfactory in ethanol productivity and ethanol tolerance, is also preferable.

The yeast strains capable of mannitol assimilation of the present invention can be cultured to produce ethanol. Such yeast strains are cultured in accordance with a common technique employed for yeast culture. Mannitol may be added to a known medium.

A starting material, mannitol, may be added to a final concentration of 1% to 10% (w/v), preferably 1% to 5% (w/v), and more preferably 2% to 5% (w/v). Also, mannitol may be added with the elapse of time during culture.

Culture is conducted under aerobic conditions, such as via shake culture or aeration-agitation culture, at 20° C. to 40° C., and preferably 28° C. to 32° C., and at a pH of 5.6 to 9.0, and preferably at a pH of 5.6 to 8.4, for several hours to several days (e.g., 4 to 7 days).

The pH level in a medium may be adjusted with the use of an inorganic or organic acid, an alkaline solution, or the like. During culture, antibiotics, such as kanamycin or penicillin, may be added to the medium, according to need.

At the time of culture, yeast strains may be added so as to adjust $A_{600}$ (i.e., the absorbance at 600 nm) to 0.05 to 11 (e.g., 0.05 to 5, preferably 0.05 to 0.2, and more preferably 0.1) when culture is initiated.

By conducting culture under the conditions described above, 0.1% (w/v) or more, preferably 0.3% (w/v) or more, more preferably 1% (w/v) or more, more preferably 3% (w/v) or more, and particularly preferably 3.5% (w/v) or more ethanol can be accumulated in a medium. When culture is conducted in a medium containing 10% (w/v) mannitol, for example, 3% (w/v) or more and particularly preferably 3.5% (w/v) or more ethanol can be accumulated in the end.

In addition, yeast strains grow via culture, and $A_{600}$ is increased to about 0.1 to 33 when culture is completed.

Further, culture can be conducted with the use of a residue of starting materials obtained when ethanol is produced with the use of microorganisms capable of alginic acid assimilation from alginic acid contained in brown algae or the like. Such residue contains mannitol, which was not assimilated by microorganisms capable of alginic acid assimilation.

Examples of starting materials (i.e., brown algae (Phaeophyceae)) include *Laminaria japonica, Undaria pinnatiflida, Nemacystus decipiens, Sargassum fulvellum*, and *Sargassum fusiforme*. An example of a microorganism capable of alginic acid assimilation is the ethanol-producing *Sphingomonas* sp. A1 strain into which a gene encoding an enzyme (pyruvic acid decarboxylase or alcohol dehydrogenase) associated with ethanol production of bacteria such as *Zymomonas mobilis* has been introduced. For example, the residue may contain about 0.5% to 2% (w/v) ethanol and about 1% to 10% (w/v) mannitol. The yeast strains capable of mannitol assimilation of the present invention are added to such residue and cultured. In such a case, yeast strains may be added so as to adjust $A_{600}$ (i.e., the absorbance at 600 nm) to 0.05 to 11 (e.g., 1 to 11, preferably 1 to 5, and more preferably 1 to 3). Culture is conducted under aerobic conditions, such as via shake culture or aeration-agitation culture, at 20° C. to 40° C., and preferably 28° C. to 32° C., and at a pH of 5.6 to 9.0, and preferably at a pH of 5.6 to 8.4, for several hours to several days (e.g., 4 to 7 days). For example, the ethanol concentration may reach 1% to 5% (w/v) after culture has been conducted for 4 to 7 days. The value obtained by subtracting the amount of the produced alcohol from the amount of ethanol in the residue represents the amount of ethanol that was newly produced using yeast strains capable of mannitol assimilation. The ethanol concentration is increased to 1.5 to 3 times and preferably to about twice the concentration in the residue with the aid of ethanol produced by the yeast strains capable of mannitol assimilation. In the present invention, a method of producing ethanol from mannitol in the residue with the use of the residue of the starting materials used for ethanol production from alginic acid and then obtaining a large quantity of ethanol from mannitol is referred to as "two-step fermentation."

When producing ethanol from brown algae, alginic acid and mannitol may be extracted from brown algae and used as carbon sources to conduct culture. Alternatively, brown algae may be fractured, and culture may be conducted with the use of such fractured product (including alginic acid and mannitol) as a carbon source. In any case, brown algae do not contain lignin, unlike ligneous biomass. Thus, alginic acid and mannitol can be extracted and used under relatively milder conditions than those applied for the processing of ligneous biomass or the like. Since ethanol production from corn starch requires a step of saccharification, ethanol production from alginic acid and mannitol does not require a step of saccharification. Thus, the latter form of ethanol production is advantageous over the former.

Ethanol can be recovered via distillation. In addition, ethanol can be quantified via known techniques, such as a method involving the use of alcohol dehydrogenase or gas chromatography.

The yeast strains can be immobilized to produce ethanol. Examples of methods for immobilizing microorganisms include the inclusion method, the cross-linking method, and the carrier-binding method. According to the inclusion method, microorganisms are included in fine lattices of polymer gel or covered by a semi-permeable polymer membrane. According to the cross-linking method, microorganisms are crosslinked to each other with a reagent having two or more functional groups (i.e., a polyfunctional cross-linking agent). According to the carrier-binding method, enzymes are bound to water-insoluble carriers. Examples of immobilization carriers include glass beads, silica gel, polyurethane, polyacrylamide, polyvinyl alcohol, carragheenan, alginic acid, agar, and gelatin.

EXAMPLES

The present invention is described in greater detail with reference to the following examples, although the present invention is not limited to these examples.

Experimental Method

Medium and Culture

A carbon-source-free medium (pH 5.6) contains 0.67% (w/v) yeast nitrogen base (w/o amino acids, Difco), 0.69 g/l-Leu dropout supplement (Clontech), and 100 mg/l L-leucine. Glucose synthetic medium, mannitol synthetic medium, glycerol synthetic medium, and laminarin synthetic medium are prepared by adding glucose (final concentration: 2% (w/v)), mannitol (final concentration: 2% (w/v)), glycerol (final concentration: 3% (w/v)), and laminarin (final concentration: 2% (w/v); derived from *Laminaria digitata*; Product number: L9634, Sigma) to a carbon-source-free medium. YP medium (pH 5.6) contains 1% (w/v) yeast extract and 2% (w/v) trypton. The pH level was adjusted with HCl. YPD, YPM, and YPG media were prepared by adding glucose (final concentration: 2% (w/v)), mannitol (final concentration: 2% (w/v)), and glycerol (final concentration: 3% (w/v)) to YP medium, respectively. Carbon sources and other components were separately sterilized in autoclaves (and laminarin was sterilized through a filter) and then mixed. These media were prepared using 2×YP (pH 5.6, 2×-concentrated YP medium) unless otherwise specified. The pH level of the YPM medium was 5.7. 10×YP medium (pH 5.6, 10×-concentrated YP medium) was subjected to sterilization through a filter instead of sterilization in an autoclave. The pH level of the YPM medium was 7.8 when 2×YP medium (pH 8.0, adjusted with NaOH) was used. For a solid medium, agar (Nacalai Tesque, Inc.) was added thereto to a final concentration of 2% (w/v) therein. Culture was conducted at 30° C. Cells were sowed in a liquid medium to adjust $A_{600}$ to 0.1, and culture with the use of YPD, YPM, and YP liquid media was conducted via shaking at 95 strokes per minute (spm) in a 100-ml triangular flask containing 50 ml of liquid medium, unless otherwise specified. When preculture was conducted in a solid medium, cells on the medium were suspended in sterilized water, and the resulting cell suspension was sowed in a liquid medium.

Yeast strains were processed with 25 µg/ml ethidium bromide to prepare the $\rho^0$ strains that had lost the mitochondrial genome and viability in YPG solid medium (Fox et al., 1991, Methods Enzymol., 194, 149-165). Strains having the normal mitochondrial genome are referred to as $\rho^+$ strains. Anaerobic culture was conducted by converting the atmosphere of a square jar (Mitsubishi Gas Chemical Company, Inc.) into the anaerobic atmosphere with AnaeroPack-Anaero (Mitsubishi Gas Chemical Company, Inc.). The transgenic ethanol-producing *Sphingomonas* sp. A1 strains (the EPv104 strains described below) were cultured using a 5% alginic acid medium in accordance with a relevant report (Takeda et al., 2011, Energy Environ. Sci., 4, 2575-2581). At the time of initiation of culture, mannitol powder was added to the resultant to a concentration of 2% or 5% (w/v). The supernatant in the culture solution 3 days after the initiation of culture was obtained via centrifugation, and it was designated as a residue of ethanol fermentation from alginic acid using the A1 strains (containing mannitol).

Strains

In this example, the 48 yeast strains conserved at the laboratories shown in Table 1 were used in order to search for yeast strains capable of mannitol assimilation. The $\rho^0$ strains of *Saccharomyces paradoxus* NBRC 0259 and *S. cerevisiae* BY4742 were prepared via processing with ethidium bromide (Fox et al., 1991, Methods Enzymol., 194, 149-165). These yeast strains were cultured on YPD liquid medium and then stored at −80° C. in the presence of 17% glycerol. The EPv104 strains were used as the ethanol-producing A1 strains (Takeda et al., 2011, Energy Environ. Sci., 4, 2575-2581). The EPv104 strains exhibit the highest ethanol productivity from alginic acid, and they were prepared by introducing 8 copies of the pyruvic acid decarboxylase gene (pdc) derived from *Zymomonas mobilis* and a copy of the alcohol dehydrogenase gene (adhB) derived from *Zymomonas mobilis* into the lactic acid dehydrogenase gene-deficient strains of the *Sphingomonas* sp. A1 strains through the promiscuous vector (pKS13) (Takeda et al., 2011, Energy Environ. Sci., 4, 2575-2581).

TABLE 1

Yeast strains subjected to inspection of the capacity for mannitol assimilation

| Yeast names | AKU No. | Other numbers |
|---|---|---|
| *Saccharomyces cerevisiae* BY4742 | | ATCC 201389 |
| American yeast (Fleishman baker's yeast) | AKU 4001 | |
| Bass Bier Hefe (Burton on Trent No. 1) | AKU 4002 | |
| Hefe logos van Laer | AKU 4003 | |
| American yeast (American whisky yeast) | AKU 4004 | |
| *Saccharomyces sake* Chuyu | AKU 4011 | |
| *Saccharomyces sake* Hozan | AKU 4013 | |
| *Saccharomyces sake* Ozeki | AKU 4014 | |
| *Saccharomyces sake* Sakaizumi | AKU 4016 | |
| *Saccharomyces sake* Fukumusume | AKU 4017 | |
| *Saccharomyces sake* Unryu | AKU 4019 | |
| *Saccharomyces sake* Sawanotsuru | AKU 4022 | |
| Pekahefe | AKU 4030 | |
| Wine yeast | AKU 4036 | |
| Beer yeat (Kirin) | AKU 4037 | |
| Baker's yest (Oriental) | AKU 4039 | |
| Munchen beer yest | AKU 4042 | |
| *Saccharomyces carsvergensis* | AKU 4044 | |
| *Saccharomyces cerevisiae* | AKU 4100 | |
| *Saccharomyces logos* | AKU 4101 | |
| *Kazachstania unispora* | AKU 4106 | NBRC 0215 |
| *Saccharomyces fragilis* | AKU 4108 | IFO 0228 |
| *Saccharomyces sake* | AKU 4110 | Kyokai No. 6 |
| *Saccharomyces sake* | AKU 4111 | Kyokai No. 7 |
| *Saccharomyces cerevisiae* | AKU 4136 | NBRC 1346 |
| *Saccharomyces cerevisiae* | AKU 4150 | IAM 4512 |
| *Schizosaccharomyces pombe* | AKU 4220 | NBRC 0346 |
| <u>*Saccharomyce* paradoxus</u> [a] | <u>AKU 4135</u> | <u>NBRC 0259</u> |
| <u>*Zygosaccharomyce* japonicus</u> | <u>AKU 4242</u> | <u>IFO 0595</u> |
| <u>*Pichia* polymorpha</u> | <u>AKU 4250</u> | <u>IFO 0195</u> |
| *Pichia farinosa* | AKU 4262 | NBRC 0193 |
| <u>*Pichia* haplophila</u> | <u>AKU 4263</u> | <u>NBRC 0947</u> |
| <u>*Pichia* saitoi</u> | <u>AKU 4266</u> | <u>IAM 4945</u> |
| *Hansenula saturnus* | AKU 4301 | IFO 0177 |
| <u>*Kuraishia* capsulata</u> [a] | <u>AKU 4305</u> | <u>NBRC 0721</u> |
| *Wickerhamomyces silvicola* | AKU 4313 | NBRC 0807 |
| <u>*Kuraishia* capsulata</u> [a] | <u>AKU 4326</u> | <u>NBRC 0974</u> |
| <u>*Ogataea* glucozyma</u> [a] | <u>AKU 4330</u> | <u>NBRC 1472</u> |
| <u>*Ogataea* minuta</u> [a] | <u>AKU 4332</u> | <u>NBRC 1473</u> |
| <u>*Debaryomyces* hansenii</u> | <u>AKU 4357</u> | <u>IFO 0023</u> |
| <u>*Debaryomyce* hansenii</u> [a] | <u>AKU 4359</u> | <u>NBRC 0794</u> |
| *Naumovia castellii* | AKU 4127 | NBRC 0285 |
| *Hanseniaspora valbyensis* | AKU 4405 | NBRC 0115 |
| *Sporidiobolus salmonicolor* | AKU 4440 | NBRC 1035 |
| <u>*Yarrowia* lipolytica</u> | <u>AKU 4598</u> | <u>NBRC 0746</u> |
| *Yarrowia lipolytica* | AKU 4599 | NBRC 1195 |
| *Candida solani* | AKU 4612 | NBRC 0762 |
| *Candida albicans* | AKU 4633 | NBRC 1269 |

Strains that had grown more satisfactorily in mannitol synthetic solid and liquid media than in carbon source-free solid and liquid media were underlined
[a] 6 Ethanol-producing yeast strains Measurement of Ethanol Concentration The ethanol concentration was measured using F-kit ethanol (Roche Diagnostics K. K., Tokyo, Japan) in accordance with the protocols included in the kit.

Analysis of ITS-5.8S rDNA Nucleotide Sequence

Amplification of the ITS-5.8S rDNA nucleotide sequence of the *S. paradoxus* NBRC 0259 strain via PCR and nucleotide sequence analysis were consigned to TechnoSuruga Laboratory Co., Ltd.

Results and Discussion

Searching for Ethanol-Producing Yeast Capable of Mannitol Assimilation

Figure 2A:
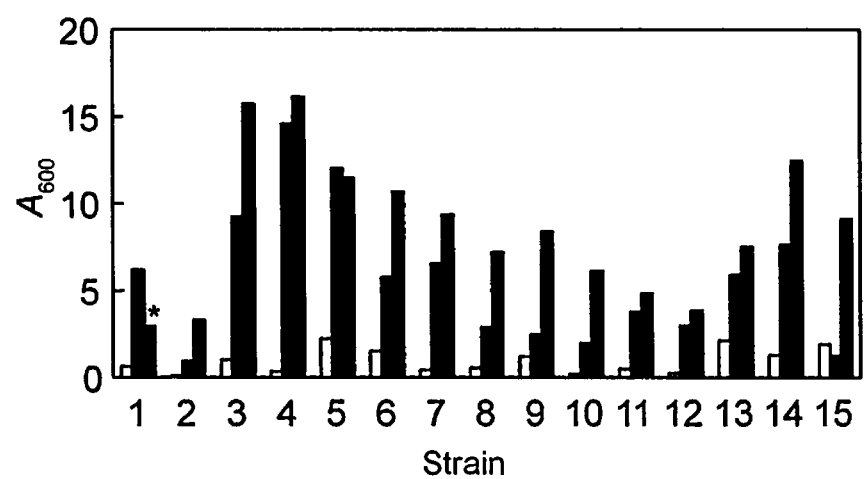
FIG. 2A shows growth of yeast strains capable of mannitol assimilation in a carbon-source-free liquid medium (white), a mannitol synthetic liquid medium (fine parallel lines), and a glucose-synthetic liquid medium (black). The yeast strain numbers were as follows: 1: *S. paradoxus* NBRC 0259; 2: *Z. japonicus* IFO 0595; 3: *P. polymorpha* IFO 0195; 4: *P. farinosa* NBRC 0193; 5: *P. haplophila* NBRC 0947; 6: *P. saitoi* IAM 4945; 7: *H. saturnus* IFO 0177; 8: *K. capsulata* NBRC 0721; 9: *K. capsulata* NBRC 0974; 10: *O. glucozyma* NBRC 1472; 11: *O. minuta* NBRC 1473; 12: *D. hansenii* IFO 0023; 13: *D. hansenii* NBRC 0794; 14: *Y. lipolytica* NBRC 0746; and 15: *S. cerevisiae* BY4742 (control). The *S. paradoxus* NBRC 0259 strain (Strain 1) exhibited strong aggregability in a glucose-synthetic liquid medium (*) and weak aggregability in mannitol-synthetic medium.
Figure 2B:
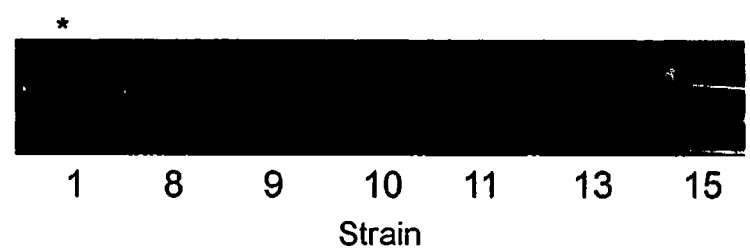
FIG. 2B shows growth of ethanol-producing yeast strains capable of mannitol assimilation in a glucose-synthetic liquid medium. The yeast strain numbers are the same as those shown in FIG. 2A (i.e., yeast strain numbers 1: *S. paradoxus* NBRC 0259; 8: *K. capsulata* NBRC 0721; 9: *K. capsulata* NBRC 0974; 10: *O. glucozyma* NBRC 1472; 11: *O. minuta* NBRC 1473; 13: *D. hansenii* NBRC 0794; and 15: *S. cerevisiae* BY4742). The *S. paradoxus* NBRC 0259 strain (Strain 1) exhibited strong aggregability in a glucose-synthetic liquid medium (*).
Figures 1, 2C:
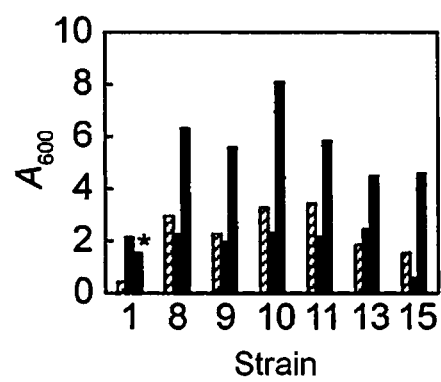
Figures 2, 2C:
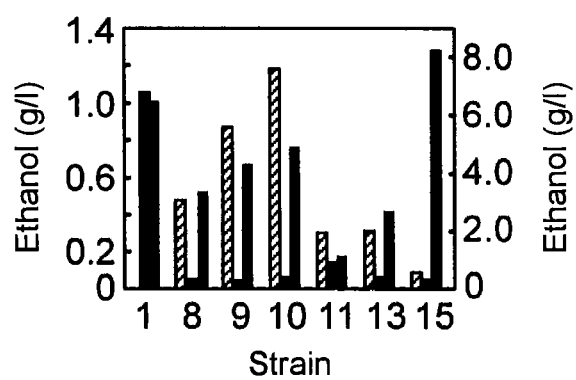

The results for searching of ethanol-producing yeast strains capable of mannitol assimilation are shown in FIG. 2.

The 48 yeast strains conserved at the laboratory of the present inventors that had been grown on YPD solid medium (Table 1) were suspended in sterilized water, 5 μl of the suspension was spotted onto synthetic solid media (carbon-source-free medium, glucose synthetic medium, and mannitol synthetic medium), and the cells were cultured for 5 days. As a result of visual observation, all strains were found to have satisfactorily grown in the glucose synthetic solid medium; however, substantially no strains were found to have grown in the carbon-source-free solid medium. Also, growth of the 14 strains indicated with underlining in Table 1 (hereafter, referred to as "yeast strains capable of mannitol assimilation") was found to be more satisfactory in the mannitol synthetic solid medium than in the carbon-source-free solid medium. Similar growth conditions were observed in a liquid medium (FIG. 2A). The growth of the *S. cerevisiae* BY4742 strain derived from S288C incapable of mannitol assimilation (hereafter referred to as the "BY4742" strain") (Brachmann et al., 1998, Yeast 14, 115-132; Quain and Boulton, 1987, J. Gen. Microbiol., 133, 1675-1684) in mannitol synthetic solid and liquid media and was not as satisfactory as that in carbon-source-free solid and liquid-containing media (FIG. 2A). Among such 14 strains, 7 strains (i.e., *P. polymorpha* IFO 0195, *P. farinosa* NBRC 0193, *P. haplophila* NBRC 0947, *P. saitoi* IAM 4945, *H. saturnus* IFO 0177, *D. hansenii* IFO 0023, and *Y. lipolytica* NBRC 0746) formed membranes in mannitol and glucose synthetic liquid media. The *S. paradoxus* NBRC 0259 strain (hereafter, referred to as "the NBRC 0259 strain") exhibited aggregability in the glucose liquid medium (FIG. 2B). Such strains also exhibited some aggregability in the mannitol synthetic liquid medium.

Figure 2D:
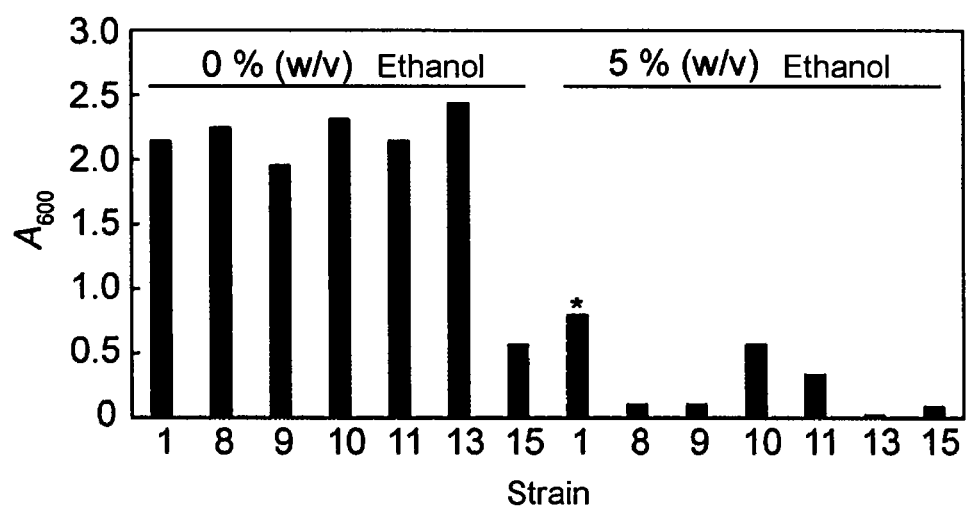
FIG. 2D shows growth of ethanol-producing yeast strains capable of mannitol assimilation in the presence of 5% (w/v) ethanol in a mannitol synthetic liquid medium. The strains that had been precultured on YPD solid medium were subjected to static culture (0 spm) in 1.0 ml of medium for 3 days. The yeast strain numbers are the same as those shown in FIG. 2B. The *S. paradoxus* NBRC 0259 strain (Strain 1) exhibited aggregability in the presence of 5% (w/v) ethanol (*).

Subsequently, the BY4742 strain (the control strains) and 14 yeast strains capable of mannitol assimilation were subjected to static culture in mannitol synthetic liquid medium for 3 days, and the ethanol concentration in the supernatant of the culture solution was measured. Among them, 6 strains (i.e., NBRC 0259, *K. capsulata* NBRC 0721, *K. capsulata* NBRC 0974; *O. glucozyma* NBRC 1472, *O. minuta* NBRC 1473, and *D. hansenii* NBRC 0794, hereafter, these strains are referred to as the "ethanol-producing yeast strains capable of mannitol assimilation") produced at least 44 mg/l ethanol (FIG. 2C-2). The other 8 strains exhibited ethanol productivity as low as 7 mg/l or less. The ethanol productivity of the NBRC 0259 strains from mannitol was significantly higher than that of the other strains (FIG. 2C-2). The 6 strains mentioned above and the BY4742 strain were subjected to static culture in the glucose-synthetic liquid medium, the laminarin synthetic liquid medium, and the mannitol synthetic liquid medium each containing 5% (w/v) and 7% (w/v) ethanol for 3 days (FIGS. 2C-1, 2C-2, and 2D). The ethanol productivity of such 6 strains from glucose was higher than that from mannitol (FIG. 2C-2). The NBRC 0259 strain exhibited the highest ethanol productivity from glucose among such 6 strains. Five strains other than the NBRC 0259 strain also exhibited ethanol productivity from laminarin (FIG. 2C-2). As a result of culture in the mannitol synthetic medium for 3 days, such 6 strains did not exhibit viability in the presence of 7% (w/v) ethanol. In the presence of 5% (w/v) ethanol, however, the NBRC 0259 strain, the *K. capsulata* NBRC 0974 strain, and the *O. glucozyma* NBRC 1472 strain exhibited growth (FIG. 2D). In the presence of 5% (w/v) ethanol, the NBRC 0259 strain exhibited aggregability.

Oxygen Requirement for Mannitol Assimilation

Figure 3A:
FIG. 3A shows the oxygen requirement for mannitol assimilation, and it shows viability of the BY4742 (BY) and NBRC 0259 (NB) $\rho^0$ and $\rho^+$ strains under normal atmospheric conditions ($+O^2$) and under anaerobic conditions ($-O^2$) in mannitol, glucose, and glycerol synthetic solid media (cultured for 4 days).
Figure 3B:
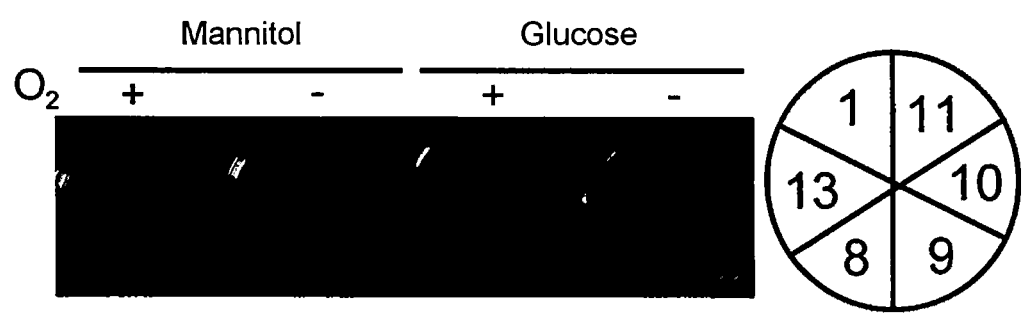
FIG. 3B shows the oxygen requirement for mannitol assimilation, and it shows viability of yeast strains capable of mannitol assimilation under normal atmospheric conditions ($+O^2$) and under anaerobic conditions ($-O^2$) in mannitol and glucose synthetic solid media. The strains that had been precultured in YPM solid medium were streaked on each medium and then cultured for 4 days. The yeast strain numbers are the same as those shown in FIG. 2B.

The oxygen requirement for mannitol assimilation is shown in FIG. 3.

In order to determine whether or not the 6 ethanol-producing yeast strains capable of mannitol assimilation found in this example require oxygen for mannitol assimilation, these strains were processed with ethidium bromide in an attempt to prepare $\rho^0$ strains. As a result, $\rho^0$ strains of only the NBRC 0259 strain was prepared. Thus, growth in a synthetic medium was inspected under anaerobic and aerobic conditions with the use of the $\rho^0$ and $\rho^+$ strains of NBRC 0259 and BY4742. As a result, the NBRC 0259 strain was found to require oxygen and respiration capacity in order to grow in the mannitol synthetic medium (FIG. 3A), and such finding was consistent with the report that had already been made (Quain and Boulton, 1987, J. Gen. Microbiol. 133, 1675-1684). In addition, the $\rho^+$ strains thereof were found to grow under an ordinary atmosphere and in YPG and YPM solid media, although the $\rho^0$ strains did not grow (data omitted). The results indicate that NBRC 0259 $\rho^+$ strains (having the capacity for mannitol assimilation) can be selected using YPM solid medium.

The viability of 5 strains ($\rho^+$ strains) other than the NBRC 0259 strain in synthetic media was inspected under aerobic and anaerobic conditions. As a result, these strains were found to exhibit no viability in mannitol synthetic medium (FIG. 3B) or YPM solid medium (not shown) under anaerobic conditions. The results demonstrate that the 5 strains other than the NBRC 0259 strain require oxygen for mannitol assimilation. When mannitol is assimilated using yeast, an excess NADH molecule is generated during the process of conversion of mannitol into fructose with the action of mannitol dehydrogenase, and it is considered that oxygen is required for regeneration of $NAD^+$ from such excess NADH (FIG. 1) (Quain and Boulton, 1987, J. Gen. Microbiol. 133, 1675-1684). It was deduced that the ethanol-producing yeast strains capable of mannitol assimilation required oxygen for growth in mannitol synthetic medium or YPD medium for the same reason. In contrast, the 5 strains other than the NBRC 0259 strain did not exhibit viability in glucose synthetic medium (FIG. 3B) or YPD solid medium (not shown) under anaerobic conditions. This suggests that the 5 strains other than the NBRC 0259 strain may assimilate glucose in a manner somewhat different from that of the NBRC 0259 strain.

Figures 1, 4A:
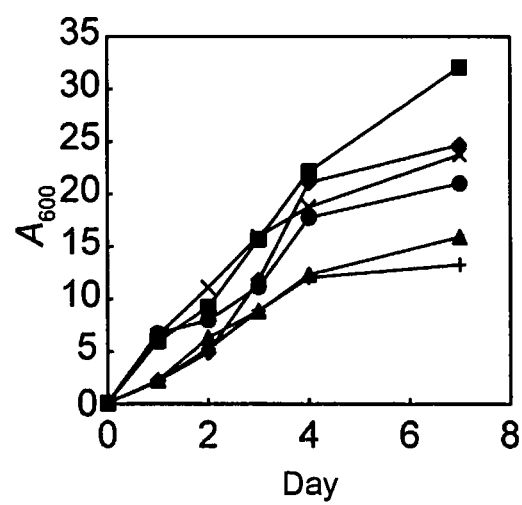
Figures 2, 4A:
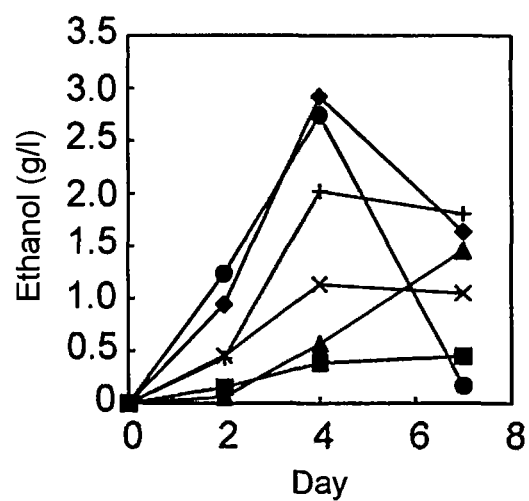

Ethanol Production Using Ethanol-Producing Yeast Strains Capable of Mannitol Assimilation FIG. 4 shows ethanol production using the ethanol-producing yeast strains capable of mannitol assimilation.

The ethanol productivity of the 6 ethanol-producing yeast strains capable of mannitol assimilation was inspected in greater detail. YPM medium was used as a basal medium herein below. Since the 6 strains mentioned above required oxygen for the growth in mannitol medium (FIG. 3), viability and ethanol productivity thereof were inspected using YPM liquid medium via shake culture at 95 spm (FIGS. 4A-1 and 4A-2). As a result, the NBRC 0259 strain and the *O. glucozyma* NBRC 1472 strain were found to exhibit high productivity. However, both strains, and the *O. glucozyma* NBRC 1472 strain in particular, exhibited a significantly lowered ethanol concentration in the culture solution after long-term culture. The ethanol productivity of the *D. hansenii* NBRC 0794 strain was the lowest.

Subsequently, growth (FIG. 4B) and ethanol productivity of the 6 strains in a fermentation residue containing 2% (w/v) mannitol were inspected for the purpose of ethanol production from a residue of ethanol fermentation (containing mannitol) from alginic acid using the A1 strain (i.e., two-step fermentation). The fermentation residue was weakly alkaline with a pH of 8.64. 10×YP medium (pH 5.6) was added thereto in an amount that was one tenth of the volume thereof (and the initial pH level was 7.3 consequently) and culture was initiated. The initial ethanol concentration was 9.6 g/l. However, only the NBRC 0259 strain and the *D. hansenii* NBRC 0794 strain exhibited growth. All the ethanol concentrations in the culture supernatant were lowered to levels below the initial ethanol concentration 7 days after the initiation of culture. Further, the NBRC 0259 strain exhibited aggregability. The reason for the weak viability in the fermentation residue was deduced to be as follows. Since all 6 strains grew in a weakly alkaline YPM medium (pH 7.8) (FIG. 4B), the pH level of the residue (pH 7.3) was not the cause. That is, some components in the fermentation residue inhibited growth. While the *D. hansenii* NBRC 0794 strain exhibited viability in the same fermentation residue, ethanol productivity thereof from mannitol was the lowest (FIGS. 4A-1 and 4A-2).

Figure 4B:
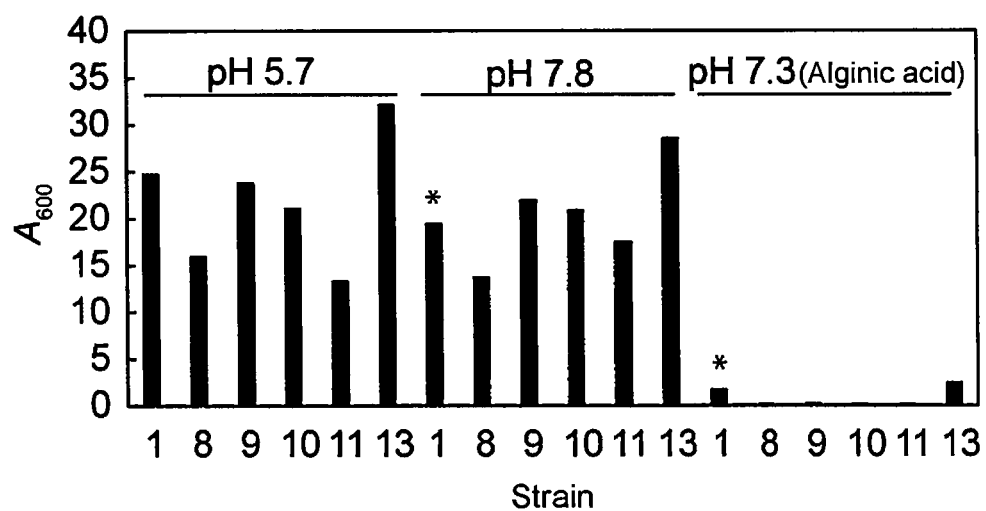
FIG. 4B shows growth 4 days after the initiation of culture on YPM liquid medium (pH 5.7), alkalescent YPM liquid medium (pH 7.8), and a residue of ethanol fermentation from alginic acid using the A1 strain (containing 2% (w/v) mannitol; pH 7.3 (alginic acid)). Culture was conducted in the same manner as with the conditions employed in FIG. 4A, except for the medium components. The cells that had been precultured on YPM solid medium were used. The yeast strain numbers are the same as those shown in FIG. 2B. Weak aggregation was observed in alkalescent YPM liquid medium (such aggregation being similar but weaker than that observed in YPD liquid medium) and aggregation was observed in the residue of fermentation (finely granular aggregate) (*).

Based on the results attained above, the NBRC 0259 strain was determined to be the most advantageous strains among the 6 strains due to high ethanol productivity from glucose and mannitol, ethanol tolerance, and viability in a residue of ethanol fermentation from alginic acid using the A1 strain, even though the NBRC 0259 strain did not exhibit ethanol productivity from laminarin (FIGS. 2 and 4). The *O. glucozyma* NBRC 1472 strain was considered to be the second-best strains in terms of ethanol productivity from laminarin, high ethanol productivity from glucose and mannitol, and ethanol tolerance (FIGS. 2 and 4). However, the NBRC 1472 strain was disadvantageous in that the ethanol concentration in the culture solution would be drastically lowered after long-term culture (FIG. 4A-2) and such strains were not viable in the fermentation residue (FIG. 4B). Further, ethanol production from mannitol of the *S. cerevisiae* polyploid BB1 strain and the *P. angophorae* strain, ethanol productivity from mannitol of which had been reported, has not been reported as thoroughly as described in the present example. In addition, ethanol tolerance and viability in a residue of ethanol fermentation from alginic acid are also unobvious (Horn et al., 2000, J. Ind. Microbiol. Biotechnol., 24, 51-57; Quain and Boulton, 1987, J. Gen. Microbiol., 133, 1675-1684). For these reasons, the present inventors decided to use the NBRC 0259 strain for the study below. The ITS-5.8S rDNA nucleotide sequence of the NBRC 0259 strain used in this study exhibited 100% homology (817/817) with the ITS-5.8S rDNA nucleotide sequence of the *S. paradoxus* NBR 0259 strain (Genbank: D89890), which is registered with the database. Meanwhile, it exhibited 98.9% homology (815/824) with the ITS-5.8S rDNA nucleotide sequence of the *S. cerevisiae* S288C strain (Genbank: BK006945).

Ethanol Production from Mannitol Using the NBRC 0259 Strain

FIG. 5 shows ethanol production from mannitol using the NBRC 0259 strain.

Figure 5A:
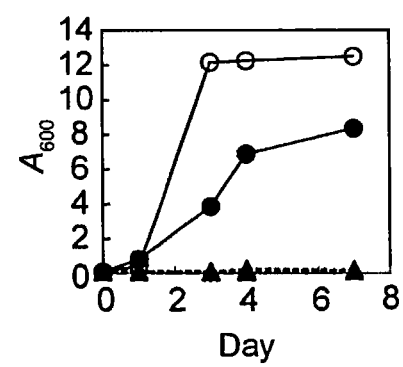
FIG. 5A shows growth of the NBRC 0259 strain in a mannitol synthetic liquid medium. The NBRC 0259 $\rho^+$ strain (YPM solid medium-derived) (solid line: ●○) and the control BY4742 $\rho^+$ strain (YPG solid medium-derived) (dotted line: ▲△) were precultured on YPD (▲●) or YPM (△○) solid medium and then subjected to shake culture at 145 spm in 1.0 ml of mannitol synthetic liquid medium. The BY4742 strain did not exhibit growth in a mannitol synthetic medium.
Figure 5B:
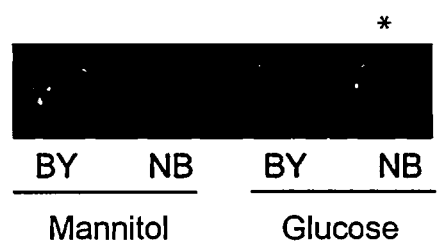
FIG. 5B shows the culture of the BY4742 (BY) strain and the NBRC 0259 (NB) strain that had been precultured on YPD solid medium and were cultured on mannitol and glucose synthetic liquid media for 4 days. Culture was conducted under the conditions described above (FIG. 5A). NBRC 0259 exhibited aggregability in a glucose-synthetic liquid medium (*).

The capacity of the NBRC 0259 strain for mannitol assimilation was further inspected. The BY4742 $\rho^+$ strain was used as the control strains. The NBRC 0259 strain that had been precultured on YPD and YPM solid media grew on the mannitol synthetic liquid medium, although the BY4742 strain did not grow (FIGS. 5A and 5B). The NBRC 0259 strain exhibited aggregability in 2% glucose liquid medium (FIG. 5B).

Figures 1, 5C:
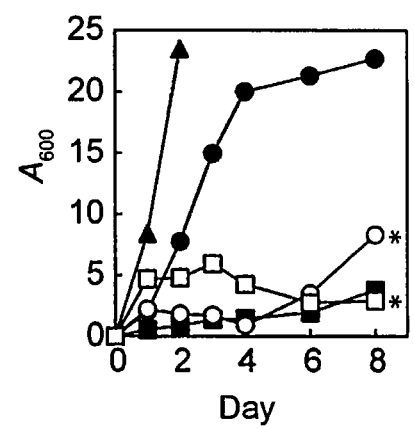
Figures 2, 5C:
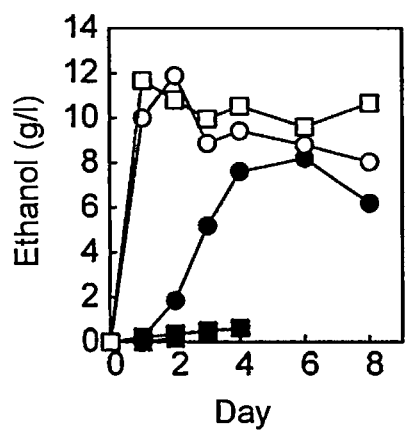
Figure 5D:
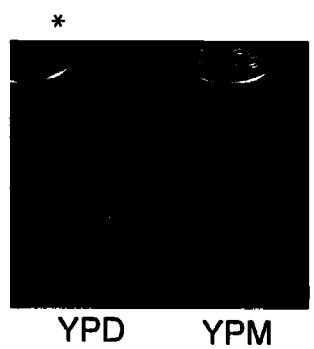
FIG. 5D shows growth of the NBRC 0259 strain in YPD and YPM liquid media. Cells form flocks and precipitate in YPD medium (*). The conditions on the first day of culture are shown.
Figure 5E:
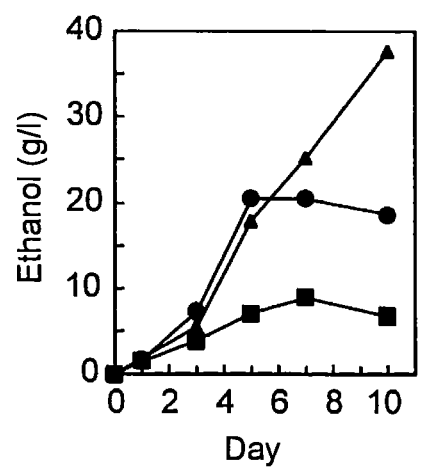
FIG. 5E shows the influence of mannitol concentration on ethanol productivity. The initial amount of cells ($A_{600}$) was set at 11, the shaking speed was set at 95 spm, and the mannitol concentration in YPM liquid medium was set at 2% (w/v: ■), 5% (w/v: ●), and 10% (w/v: ▲), respectively. The cells that had been precultured at 95 spm in YPM liquid medium for 4 days were used as the initial cells.

Subsequently, the conditions for ethanol production were inspected using YPM liquid medium. Single colonies of the NBRC 0259 strain that had grown on YPD solid medium lost viability in YPM solid and liquid media with high frequency (i.e., 5 of the 6 single-colony-derived cells lost viability among the 6 single colonies inspected). This suggests that the NBRC 0259 strain is likely to experience loss or damage of the mitochondrial genome on YPD solid medium. Thus, the NBRC 0259 $\rho^+$ strain selected on YPM solid medium was used hereinbelow. Since the NBRC 0259 $\rho^+$ strain required oxygen for mannitol assimilation (FIG. 3A), the NBRC 0259 $\rho^+$ strain was subjected to static culture at 0 spm in YPM liquid medium and shake culture at 95 spm and 145 spm, and the influence of the extent of aeration during culture on viability and on ethanol productivity was inspected. As a result, viability was found to enhance as the amount of aeration increased in accordance with the report that had already been made (FIG. 5C). The highest ethanol productivity was observed when an adequate amount of oxygen was supplied at 95 spm (i.e., ethanol productivity of 8.20 g/l for 6 days). When culture was conducted at 0 spm and 145 spm, substantially no ethanol productivity was observed (FIGS. 5C-1 and 5C-2). When glucose was used as a substrate (i.e., when YPD liquid medium is used), however, the productivity was higher than that achieved with the use of mannitol at 0 and 95 spm (approximately 12 g/l ethanol productivity each on the first day (0 spm) and the second day (95 spm)). Also, apparent aggregability was observed in YPD liquid medium (FIG. 5D).

Figure 5F:
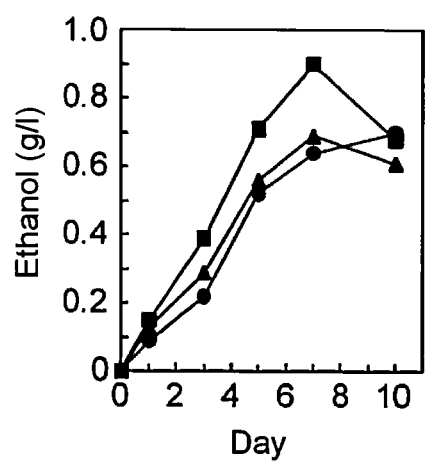
FIG. 5F shows the influence of NaCl concentration on ethanol productivity. Culture was conducted under the same conditions as with the case of FIG. 5E, except that culture was conducted in YPM liquid medium (2% (w/v) mannitol) in the presence of 0% (w/v: m), 2% (w/v: ●), and 5% (w/v: ▲) NaCl.

The influence of the mannitol concentration was inspected at a shaking speed of 95 spm. As a result, 37.6 g/l (3.8% w/v) ethanol was found to be produced at maximum from 10% (w/v) mannitol (FIG. 5E), which was the maximal amount of ethanol produced from mannitol. Also, no significant lowering was observed in ethanol productivity in the presence of 2% or 5% (w/v) NaCl (FIG. 5F). Subsequently, the influence of the preculture conditions for the NBRC 0259 strain on viability and ethanol productivity was inspected. Specifically, the strain was subjected to pre-preculture on YPM solid medium, the resultants was subjected to pre-culture on YPM or YPD liquid medium for 2 days, and the resulting strain was then subjected to washing. Thereafter, the resulting strain was sowed on YPM liquid medium. As a result, higher viability and ethanol productivity were achieved with the use of the strain that had been precultured on YPM liquid medium than with those that had been precultured on YPD liquid medium. Specifically, ethanol productivity of the former was 6.7 g/16 days after the initiation of culture; however, that of the latter was as low as 0.35 g/16 days after the initiation of culture and reached 5.2 g/112 days after the initiation of culture.

The NBRC 0259 strain was added to a medium prepared by adding 5 ml of 2×YP (pH 5.6) to 45 ml of the residue of ethanol fermentation from alginic acid containing 5% (w/v) mannitol (initial ethanol concentration: 8.5 g/l) to adjust the initial $A_{600}$ to 2.0. As a result, the ethanol concentration in the culture supernatant reached 16.9 g/l and 14.0 g/14 days and 7 days after the reaction, respectively. Specifically, 9.4 (=16.9-8.5) g/l ethanol was newly produced from mannitol in the residue via two-step fermentation. Further, expectation was made on ethanol productivity as a result of improved two-step fermentation conditions.

INDUSTRIAL APPLICABILITY

With the use of the yeast strain that produces ethanol from mannitol according to the present invention, ethanol can be effectively produced from marine biomass using large marine algae.

All publications, patents, and patent applications cited herein are incorporated herein by reference in their entirety.

The invention claimed is:

1. A method for producing ethanol using mannitol as a starting material, the method comprising culturing a yeast strain capable of mannitol assimilation and ethanol production from mannitol in a medium comprising mannitol, wherein the yeast strain is selected from the group consisting of *Saccharomyces paradoxus*, *Kuraishia capsulata*, *Ogataea glucozyma*, and *Ogataea minuta*.

2. The method for producing ethanol from mannitol according to claim 1, wherein the yeast strain capable of mannitol assimilation and ethanol production from mannitol comprises at least one property selected from the group consisting of:
(1) ethanol tolerance;
(2) viability in a residue remaining after ethanol is produced from brown algae as a starting material using microorganisms capable of alginic acid assimilation; and
(3) aggregability in the presence of glucose.

3. The method for producing ethanol from mannitol according to claim 1, wherein the yeast strains strain capable of mannitol assimilation and ethanol production from mannitol is selected from the group consisting of *Saccharomyces paradoxus* NBRC 0259 *Kuraishia capsulata* NBRC 0721, *Kuraishia capsulata* NBRC 0974, *Ogataea glucozyma* NBRC 1472, and *Ogataea minuta* NBRC 1473.

4. The method according to claim 1, wherein the yeast strain capable of mannitol assimilation and ethanol production from mannitol is cultured such that 0.1% (w/v) or more ethanol accumulates in the medium.

5. The method according to claim 4, wherein the yeast strain capable of mannitol assimilation and ethanol production from mannitol is cultured such that 3% (w/v) or more ethanol accumulates in the medium.

6. A method for producing ethanol from mannitol as a starting material remaining after ethanol is produced from brown algae, the method comprising culturing, in the mannitol remaining after ethanol is produced from brown algae, a yeast strain selected from the group consisting of *Saccharomyces paradoxus, Kuraishia capsulata, Ogataea glucozyma*, and *Ogataea minuta* and wherein the yeast strain is capable of alginic acid assimilation and ethanol production from alginic acid.

7. The method for producing ethanol from mannitol as a starting material in the residue according to claim 6, wherein the yeast strain capable of mannitol assimilation and ethanol production from mannitol has at least one property selected from the group consisting of:
(1) ethanol tolerance;
(2) viability in a residue remaining after ethanol is produced from brown algae as a starting material using microorganisms capable of alginic acid assimilation; and
(3) aggregability in the presence of glucose.

8. The method for producing ethanol from mannitol as a starting material in the residue according to claim 6, wherein the yeast strain is *Saccharomyces paradoxus.*

9. The method for producing ethanol according to claim 6, wherein the yeast strain is *Saccharomyces paradoxus* NBRC 0259.

10. A method for producing ethanol from brown algae as a starting material, the method comprising:
(i) culturing a microorganism capable of alginic acid assimilation and ethanol production from alginic acid using brown algae as a starting material to produce ethanol from alginic acid;
(ii) adding a yeast strain capable of mannitol assimilation and ethanol production from mannitol to a residue obtained in (i);
(iii) culturing the yeast strain to assimilate mannitol and produce additional ethanol.

11. The method for producing ethanol from brown algae as a starting material according to claim 10, wherein the yeast strain capable of mannitol assimilation and ethanol production from mannitol has at least one property selected from the group consisting of:
(1) ethanol tolerance;
(2) viability in a residue remaining after ethanol is produced from brown algae as a starting material using microorganisms capable of alginic acid assimilation; and
(3) aggregability in the presence of glucose.

12. The method for producing ethanol from brown algae as a starting material according to claim 10, wherein the yeast strain is a *Saccharomyces paradoxus* strain.

13. The method for producing ethanol from brown algae as a starting material according to claim 12, wherein the yeast strain is *Saccharomyces paradoxus* NBRC 0259.

* * * * *